US004001658B2

United States Statutory Invention Registration [19]

[11] Reg. Number: H1658

Love et al.

[45] Published: Jul. 1, 1997

[54] TECHNIQUE FOR AUTOMATICALLY PREPARING A DIALYSIS MACHINE AT A PREDETERMINED DATE AND TIME

[76] Inventors: Steve Love, 314 Bluebird Dr., Bailey, Colo. 80421; Eric Zimmerman, 11243 W. Dorado Ave., Littleton, Colo. 80127; Jim Rosa, 11183 Conifer Mountain Rd., Conifer, Colo. 80433; Catherine DiMuzio, 810 Medea Way, Denver, Colo. 80209

[21] Appl. No.: 484,013

[22] Filed: Jun. 7, 1995

[51] Int. Cl.[6] ..... B08B 7/04

[52] U.S. Cl. ..... 134/18; 134/22.11

[58] Field of Search ..... 134/10, 18, 22.1, 134/22.11; 422/26, 28, 116

[56] References Cited

U.S. PATENT DOCUMENTS

| | | | |
|---|---|---|---|
| 4,158,034 | 6/1979 | Riede et al. | 422/36 |
| 4,166,031 | 8/1979 | Hardy | 134/26 X |
| 4,332,264 | 6/1982 | Gortz et al. | 134/57 R |
| 5,173,125 | 12/1992 | Felding | 134/22.11 |
| 5,256,371 | 10/1993 | Pippert | 422/28 |
| 5,409,612 | 4/1995 | Maltais et al. | 210/636 |

*Primary Examiner*—Charles T. Jordan
*Assistant Examiner*—Meena Chelliah

[57] ABSTRACT

A technique for automatically cleaning, disinfecting and otherwise preparing a dialysis machine includes a method and apparatus for programming the dialysis machine to awaken from a reduced power mode at a predetermined time and perform one of several wake-up procedures (e.g., rinsing, dialysate preparation, or hot water or chemical disinfection). A wake-up time and a corresponding wake-up procedure is preferably programmed for each day of the week. If disinfection is programmed, the machine wakes up at the predetermined time to heat the water or mix the chemicals before pumping the cleaning/disinfecting liquid through the dialysis machine. The machine then rinses the cleaning/disinfecting liquid down a waste drain. If a chemical solution is utilized, the dialysis machine may be programmed to allow the chemical solution to dwell within the dialysis machine for a predetermined period before rinsing it down the drain. The apparatus includes an input/output device, a microprocessor and a non-volatile memory system for programing and storing the desired wake-up times and cleaning/disinfecting procedures. The automatic nature of the method and apparatus allow a dialysis machine operator to prepare the dialysis machine prior to leaving at the end of the day so that the machine automatically cleans and disinfects itself or starts to prepare dialysate before the start of the next day. Sensors within the dialysis machine may determine whether the machine is properly configured for the desired wake-up procedure before the operator leaves at the end of the day.

17 Claims, 5 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

TECHNIQUE FOR AUTOMATICALLY PREPARING A DIALYSIS MACHINE AT A PREDETERMINED DATE AND TIME

The present invention relates to a new technique for making up a dialysis machine at a predetermined date and time to automatically clean and disinfect the portion of the machine which produces and pumps dialysate to a dialyzer for use during a patient's dialysis treatment.

CROSS REFERENCE TO RELATED INVENTIONS

This invention is related to the inventions described in U.S. patent applications for Technique for Priming and Recirculating Fluid Through a Dialysis Machine to Prepare the Machine for Use, Ser. No. 08/481,755; Graphical Operator Machine Interface and Method for Information Entry and Selection for a Dialysis Machine, Ser. No. 08/486,944; and Technique for Using a Dialysis Machine to Disinfect a Blood Tubing Set, Ser. No. 08/481,754, all of which were filed concurrently therewith. All of these applications are further assigned to the assignee hereof. The disclosures of these applications are further incorporated herein by this reference.

BACKGROUND OF THE INVENTION

A dialysis system is used as a substitute for the natural kidney functions of a human body. The dialysis system cleans the blood of the natural accumulation of bodily wastes by separating the wastes from the blood outside or extracorporeally of the body. The separated wastes are discharged and the cleansed blood is returned to the body.

The dialysis system consists of a dialysis machine, a dialyzer, a disposable blood tubing set and a supply of chemicals for producing a dialysate solution used within the dialyzer. The dialyzer is used with the dialysis machine to separate the wastes from the blood. The dialyzer includes a porous membrane located within a closed housing which effectively separates the housing into a blood compartment and a dialysate or filtrate compartment. The blood removed from the patient flows through the disposable blood tubing set and the blood side of the dialyzer. The dialysate solution prepared from the chemicals is passed through the dialysate side of the dialyzer. The wastes from the blood pass through the membrane by osmosis, ionic transfer or fluid transport into the dialysate and, depending upon the type of dialysis treatment, desirable components from the dialysate may pass in the opposite direction through the membrane and into the blood. The transfer of the wastes into the dialysate cleanses the blood while allowing the desired components from the dialysate to enter the bloodstream.

The transfer of blood between the patient and the dialyzer occurs within a disposable blood tubing set. The blood tubing set and the dialyzer represent a closed extracorporeal path through which the patient's blood travels. The blood tubing set includes an arterial line for drawing blood from a patient and a venous line for returning the dialyzed blood to the patient. Before the blood tubing set and the dialyzer can be used in a dialysis treatment, both must be primed with a sterile saline solution to remove air from the extracorporeal circuit.

The dialysate which flows through the dialysate compartment of the dialyzer is typically prepared by the dialysis machine within a dialysate flow path of the machine. The dialysis machine mixes purified water with chemicals such as bicarbonate and acid within the dialysate flow path and heats the prepared dialysate before pumping it to the dialyzer. The resulting dialysate mixture has beneficial chemical properties which allow the dialysate to attract the waste products from the patient's blood and draw the waste products through the dialyzer membrane. However, the same chemical properties which allow the dialysate to perform its cleansing function also tend to attract microorganisms. Thus, it is typically necessary to clean and disinfect the dialysate flow path of the dialysis machine on a daily basis before any patients are connected to the dialysis machine.

The cleaning and disinfecting process may take up to several hours or more depending on the type of disinfection process used. The typical approach to cleaning and disinfecting a dialysis machine is for a worker to start the cleaning/disinfecting process early in the morning so that it will be completed prior to the arrival of the first patient. However, such an approach typically requires the worker to arrive at a very early hour, particularly since the blood tubing set and the dialyzer can not be connected to the dialysis machine and primed until after the dialysate flow path has been cleaned and disinfected.

The requirement of cleaning and disinfecting the dialysate flow path is often governed by a regulatory agency and thus can not be avoided by a hospital or dialysis clinic. Therefore, although the majority of the cleaning and disinfecting process is typically performed automatically by the dialysis machine once it has been initiated by a worker, the requirement that the process be performed each morning, together with the length of time required to perform the process, represents a substantial burden on hospitals and clinics in the form of increased labor costs.

These and other considerations have contributed to the evolution of the present invention which is summarized below.

SUMMARY OF THE INVENTION

One of the significant aspects of the present invention pertains to programming a dialysis machine to use either hot water or a chemical solution to clean and disinfect the hydraulic components used to create and pump dialysate to a dialyzer during a dialysis treatment. Another significant aspect of the present invention relates to programming a dialysis machine to perform the cleaning and disinfecting procedure at a predetermined date and time to free a dialysis machine operator from having to arrive at work at an early hour to initiate the cleaning and disinfecting process in time to prepare the dialysis machine for the first patient. A further significant aspect of the present invention relates to allowing a dialysis machine operator to perform a chemical cleaning and disinfection procedure at the end of a day and programing the dialysis machine to rinse the chemical disinfectant from the hydraulic components at a predetermined time before the start of the next day to maximize the dwell time of the chemical disinfectant within the hydraulic components.

In accordance with these and other aspects, the present invention may be generally summarized as a method of "waking up" a dialysis machine at a predetermined date and time and commanding the dialysis machine to perform one of several different cleaning/disinfecting procedures. One such procedure utilizes only hot water, and thus the dialysis machine awakens at the predetermined time to heat the water and pump the heated water through the hydraulic components of the machine. Once the heated water has completed cleaning and disinfecting the machine, the used water is directed to a waste drain for disposal. A second cleaning/disinfecting procedure requires the dialysis machine to mix a chemical cleaner and disinfectant with the water. If desired, the chemical solution may be heated by heating the water before it is mixed with the chemicals. The dialysis machine thus awakens at the predetermined time to mix the chemicals (and optionally heat the water) before pumping the chemical solution through the hydraulic components of the machine. The chemical solution may be allowed to dwell within the hydraulic lines before it is directed to the waste drain. Once the chemical solution has been disposed of, the machine will pump a water rinse through the hydraulics to ensure that the chemicals have been flushed from the hydraulic lines.

An alternative method of automatically cleaning the machine may be used when an operator elects to perform a chemical clean/disinfect procedure in the evening after the last patient of the day has been treated. In that case, the chemical cleaner and disinfectant is pumped through the dialysis machine hydraulics and allowed to dwell within the hydraulic lines overnight. The machine is thus programmed to wake up at a relatively later predetermined time to rinse the used chemical solution down the waste drain of the dialysis machine.

The present invention also comprises a method of programing a dialysis machine to awake at a predetermined time, as well as specific apparatus which allow the machine to automatically wake up and perform the desired cleaning/disinfecting procedure at the predetermined time. The method and apparatus include using a touch screen or other input/output device to store the desired wake-up dates and times in a non-volatile memory system of the machine. A microprocessor then periodically checks the real time against the next predetermined time to awaken the dialysis machine at the predetermined time and perform the desired procedure once that procedure has been retrieved from the non-volatile memory. The method also preferably includes placing the dialysis machine in a low power energy-saving mode prior to the predetermined wake-up time and after completion of the requested wake-up procedure. A number of sensors are preferably connected within the dialysis machine to indicate to the microprocessor whether the machine has been properly configured for performing the desired cleaning/disinfecting procedure at the predetermined wake-up time.

Additional steps or apparatus may be added to enhance the basic technique described above. For example, when the cleaning/disinfecting procedure has been completed, the dialysis machine may provide an indication on the touch screen or other input/output device that the machine is ready for the operator to make the final preparations for connecting a patient to the machine. Additionally, when the dialysis machine initially awakens, it may automatically perform a diagnostic self-test of its microprocessor and nonvolatile memory system before beginning the requested cleaning/disinfecting procedure.

Automatically waking up the dialysis machine so that it may perform the routine cleaning and disinfecting procedure before the arrival of the hospital or clinic staff represents a beneficial savings in labor, as well as the time and costs associated with that saved labor.

A more complete appreciation of the present invention and its scope may be obtained from the accompanying drawings, which are briefly summarized below, from the following detailed descriptions of presently preferred embodiments of the invention, and from the appended claims.

DETAILED DESCRIPTION

Figure 1:
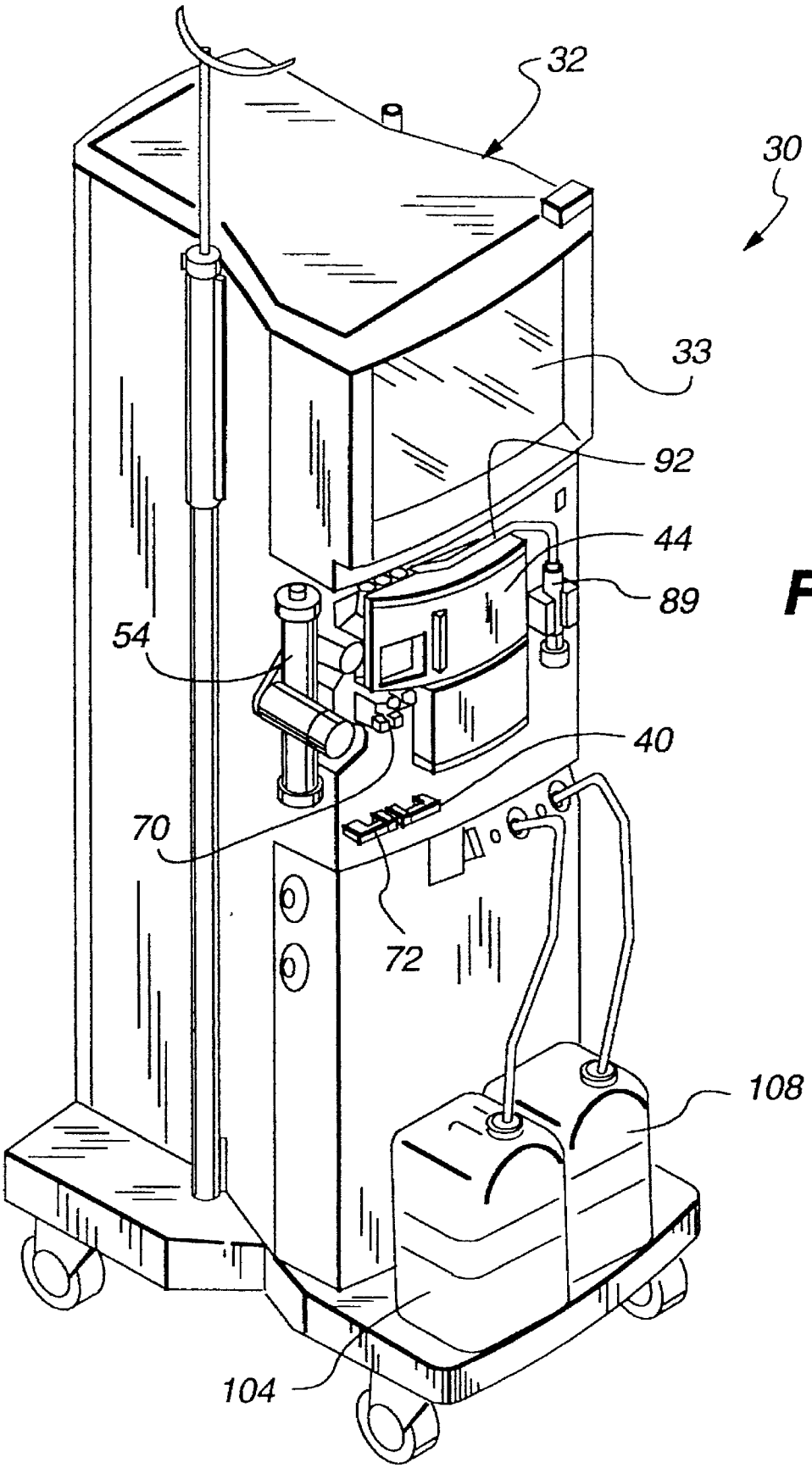
FIG. 1 is a perspective view of a dialysis machine which incorporates the present invention.
Figure 2:
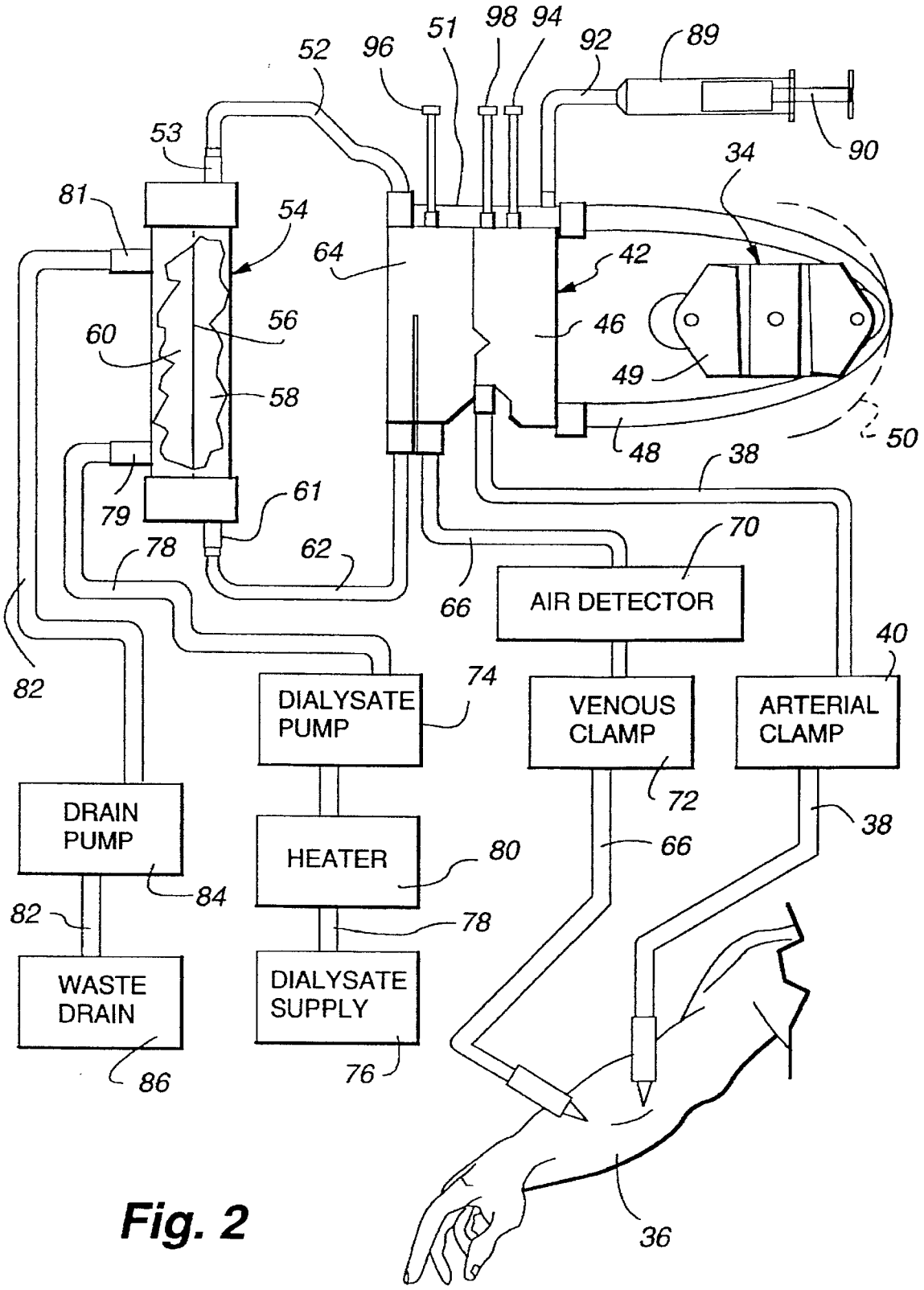
FIG. 2 is a generalized view illustrating a dialyzer, an extracorporeal blood flow path from a patient through the dialyzer, and a dialysate flow path through the dialyzer, as are present during treatment of a patient with the dialysis machine shown in FIG. 1.

An example of a dialysis machine with which the present invention may be advantageously employed is shown at 30 in FIG. 1. The dialysis machine 30 includes an enclosure 32 to which are attached, or within which are housed, those functional devices and components of the dialysis machine 30 which are generally illustrated in FIG. 2. The enclosure 30 also includes a conventional input/output ("I/O") device for controlling the machine 30, such as a touch-screen monitor 33 as shown in FIG. 1.

The dialysis machine 30 includes at least one blood pump 34 which controls the flow of blood from a patient 36. An arterial line or tubing 38 is connected through an arterial clamp 40 to a blood handling cartridge 42. The blood handling cartridge 42 is normally retained behind a door 44 (FIG. 1) of the machine 30 when used, thus the blood handling cartridge 42 is not shown in FIG. 1. The blood pump 34 also is located behind the door 44 adjacent to the cartridge 42. The blood pump 34 in dialysis machines is typically a peristaltic pump.

Blood from the patient 36 flows through an extracorporeal flow circuit when the arterial clamp 40 is open and the blood pump 34 draws blood from the patient 36. The blood passes through the arterial line 38 and into an arterial reservoir 46 of the cartridge 42. The blood pump 34 draws blood from the arterial reservoir 46 through a pump tubing 48 which is squeezed or pinched by a rotating rotor 49 against a stationary raceway 50, in the typical manner of peristaltic pumps. The blood within the pump tubing 48 which is rotationally in front of the rotor 49 is propelled through the pump tubing 48 and into a manifold 51 of the cartridge 42. A tubing 52 conducts the blood from the manifold 51 of the cartridge 42 into a blood inlet 53 of a conventional dialyzer 54. A microporous membrane or other type of dialysis medium 56 divides the interior of the dialyzer 54 into a blood chamber 58 and a dialysate chamber 60.

As the patient's blood passes through the dialyzer 54, the waste products within the blood pass through the medium 56 where they mix with the dialysate in the chamber 60. The cleansed blood then exits the dialyzer 54 through a blood outlet 61 and is then transferred through a tubing 62 to a venous reservoir 64 of the cartridge 42. Any air which might have been unintentionally introduced into the blood is collected and removed while the blood is in the venous reservoir 64. The blood exits the venous reservoir 64 through a venous tubing or line 66 which, in turn, passes through an air detector 70. The air detector 70 derives signals related to the quantity of air, if any, remaining in the venous line 66. If an excessive or dangerous amount of air is present, a venous line clamp 72 will immediately close to terminate the flow of blood through the venous line 66 before the detected air reaches the patient 36.

The enclosure 32 of the dialysis machine 30 also encloses the various elements of a dialysate flow path, shown in abbreviated form in FIG. 2. The elements of the dialysate flow path include a number of different valves (most of which are not shown) and a dialysate pump 74 which draws dialysate from a container 76 or from an internal supply of dialysate which the dialysis machine 30 has prepared from appropriate chemicals and a supply of purified water.

The dialysate pump 74 draws the dialysate from the supply 76 and delivers the dialysate through a dialysate supply tubing or line 78 to an inlet 79 of the dialysate chamber 60 of the dialyzer 54. The dialysate flows past the medium 56 where it absorbs the waste products from the blood in the blood chamber 58. Any beneficial components within the dialysate which are desired to be transferred to the blood pass through the medium 56 and enter the blood in the blood chamber 58.

Prior to reaching the dialyzer 54, a heater 80 heats the dialysate to normal human body temperature. Because the dialysate and the blood will readily transfer heat across the medium 56 within the dialyzer 54, it is important that the dialysate be at body temperature to prevent excessive heat transfer to or from the patient.

Dialysate containing the waste products exits the dialysate chamber 60 through an outlet 81 and is removed from the dialyzer 54 through a dialysate waste tubing or line 82 by operation of a waste pump 84. The waste pump 84 is operated at a lesser volumetric pumping rate compared to the volumetric pumping rate of the dialysate pump 74 when it is desired to transfer components from the dialysate into the blood by fluid transport within the dialyzer 54. The waste pump 84 is operated at a greater volumetric pumping rate compared to the volumetric pumping rate of the dialysate pump 74 when it is desired to remove fluid components from the blood by fluid transport. Both of these flow control techniques are known as ultrafiltration and are well known to those skilled in the art.

The dialysate removed from the dialyzer 54 is delivered through the waste tubing 82 to a waste drain 86. The waste drain 86 may be a separate container which receives the used dialysate and accumulated waste products, or it may simply be a drain to a public sewer. The various valves and pumps which control the dialysate flow path are referred to generally as the dialysate hydraulics.

Because the blood in the extracorporeal flow path is prone to clot, it is typical to inject an anticoagulant such as heparin into the extracorporeal flow path. The typical approach to injecting the anticoagulant is to slowly deliver it from a syringe 89. A plunger 90 of the syringe is slowly and controllably displaced into the syringe 89 by a linear driver mechanism (not shown), which is typically referred to as an anticoagulant pump. Anticoagulant from the syringe 89 is introduced into the manifold 51 of the cartridge 42 through a tubing 92 connected to the syringe as shown in FIG. 2.

Tubings 94 and 96 are respectively connected to the arterial reservoir 46 and venous reservoir 64 of the cartridge 42 as shown in FIG. 2. Clamps or caps (not shown) are connected to the ends of the tubings 94 and 96 to selectively vent accumulated air from the reservoirs 46 and 64. A saline tubing 98 is also connected to the arterial reservoir 46 so that saline may be directly administered to the patient during treatment in case of low blood pressure. Additionally, medicines or other additives may be introduced into the blood through the access tubing 94 during treatment.

The reservoirs 46 and 64 and the manifold 51 of the blood handling cartridge 42, together with the tubes 38, 48, 52, 62 and 66, are collectively referred to as a blood tubing set ("BTS"). The BTS is disposable and is typically thrown away after each dialysis treatment. Similarly, the dialyzer 54 is termed a disposable product, although it is not uncommon for a dialyzer to be reused with a single patient. A dialyzer will typically be reused by a patient who regularly visits the same clinic for dialysis treatments. Following each treatment, the dialyzer is cleaned with a sterilant and is then stored until the patient's next visit to the clinic. The dialyzer must then be thoroughly cleaned before use to ensure that the sterilant is not transferred to the patient's bloodstream during the next dialysis treatment.

The dialysate hydraulics and the disposable BTS comprise completely separate flow paths separated by the membrane or medium 56 within the dialyzer 54. Prior to each dialysis treatment, the disposable BTS must be primed and recirculated with a sterile fluid to remove the air and establish a stable flow within the BTS before the arterial line 38 is connected to a patient. A technique for automatically priming and recirculating the sterile fluid through the BTS is described in the above-referenced U.S. Patent Application entitled Technique for Priming and Recirculating Fluid Through a Dialysis Machine to Prepare the Machine for Use, and assigned to the assignee hereof. While the BTS is changed prior to each dialysis treatment, the dialysate hydraulics are typically cleaned and disinfected at the beginning of each day before the first patient is connected to the dialysis machine 30. The dialysate hydraulics shown in abbreviated fashion in FIG. 2 are shown in slightly greater detail in FIGS. 3 and 4, although many components of the dialysis hydraulics are still omitted (or have been shown in a generalized manner) for the sake of clarity.

Figure 3:
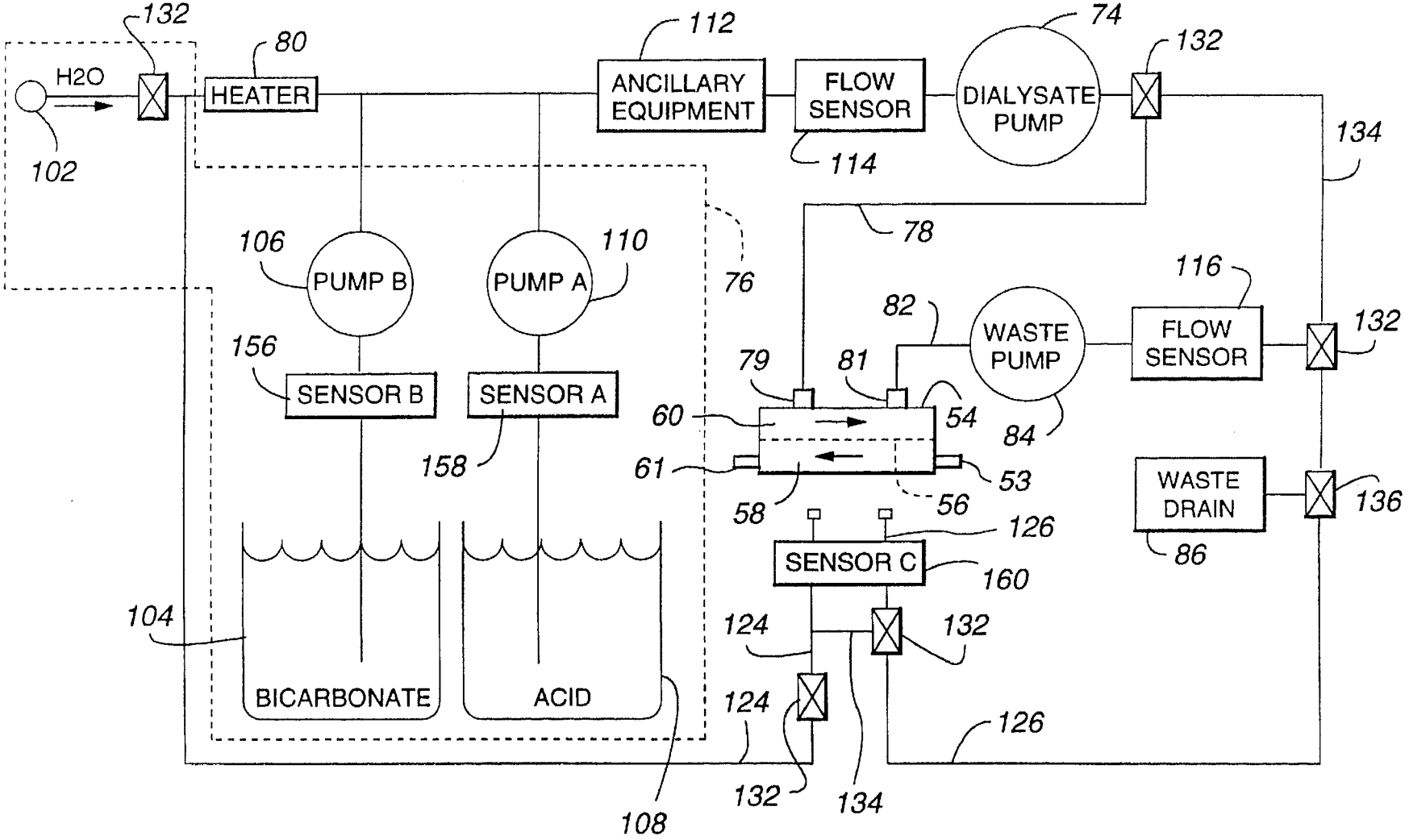
FIG. 3 is an expanded view of the dialysate flow path shown in FIG. 2 (including the dialyzer), where the extracorporeal blood flow path has been omitted for clarity.
Figure 4:
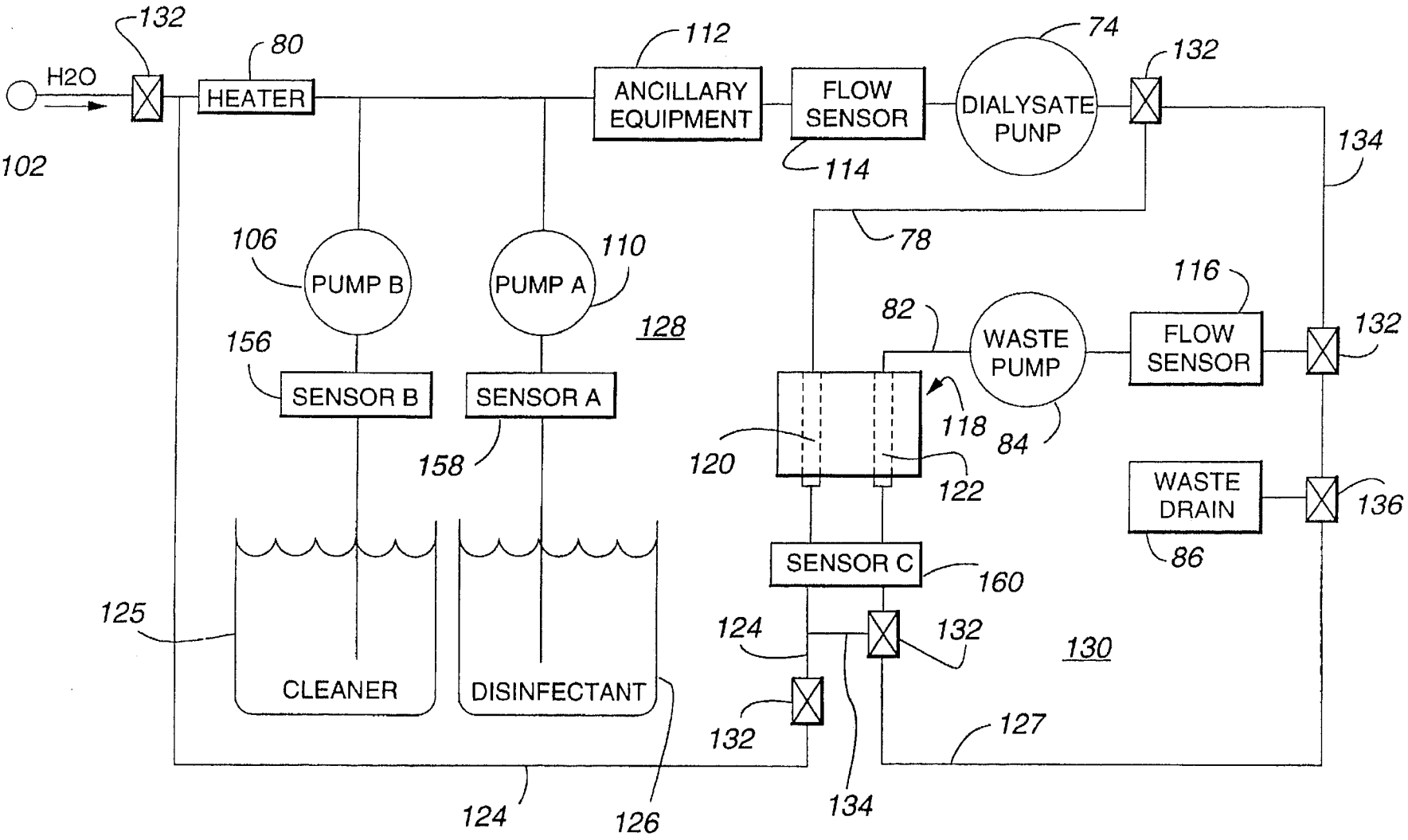
FIG. 4 is a view of the dialysate flow path similar to FIG. 3, where the dialyzer has been replaced by a bypass for the purpose of cleaning and sterilizing the dialysate flow path.

When the dialysis machine 30 creates its own supply of dialysate, as opposed to using a previously prepared supply as shown in FIG. 1, the dialysate supply 76 preferably takes the simplified form shown in FIGS. 3 and 4. The dialysate hydraulics creates the dialysate by mixing a flow of purified water from source 102 with chemicals which typically include bicarbonate and acid. Bicarbonate is pumped from a source 104 by a pump labeled at 106 as "Pump B." Similarly, acid is pumped from a source 108 by a pump labeled at 110 as "Pump A." The water is preferably heated by the heater 80 before it is mixed with the bicarbonate and acid within the dialysate line 78.

A number of various filters, sensors and other ancillary devices are shown generally at 112. A filter is typically necessary to remove any impurities from the dialysate before it enters the dialyzer 54. Additionally, the temperature, conductivity and pH level of the dialysate is sensed at 112. The sensors then control the heater 80 and the pumps 106 and 110 to maintain the temperature and composition of the dialysate within prescribed limits. A predetermined composition of the dialysate is necessary to achieve the desired level of ionic transfer between the blood and the dialysate within the dialyzer 54. Similarly, the temperature of the dialysate must be regulated to prevent excessive heat transfer to or from the patient. Other ancillary equipment that may be generally represented at 112 includes bubble traps and degassing valves to ensure that no air bubbles are sent through the dialysate line 78 to the dialyzer 54.

The dialysate pump 74 pumps the mixed dialysate through the inlet 79 and into the dialysate chamber 60 of the dialyzer 54. The dialysate within the chamber 60 cleanses the patient's blood across the membrane or medium 56 as the BTS (not shown in FIGS. 3 and 4) passes the blood through the blood chamber 58 (between the inlet 53 and the outlet 61) of the dialyzer 54. The dialysate waste pump 84 then disposes of the used dialysate by pumping it from the dialyzer outlet 81 to the waste drain 86 through the waste line 82.

As noted above, the dialysate pump 74 and the waste pump 84 may be operated at different volumetric pumping rates when it is desired to transfer components between the dialysate and the blood by fluid transport across the membrane 56 within the dialyzer 54. Flow sensors 114 and 116 measure the respective dialysate flow rates before and after passage through the dialyzer 54 to control to the pumps 74 and 84. For example, when it is desired to transfer components from the dialysate to the blood within the dialyzer 54, the waste pump 84 may be slowed until the flow sensor 116 measures a flow which is reduced a predetermined amount in relation to the flow measured by the sensor 114.

When the dialysate hydraulics are cleaned and disinfected (e.g., at the start of each day), the dialyzer 54 (FIG. 3) is replaced with a dialyzer bypass block 118 (FIG. 4). The bypass block 118 includes two separate channels 120 and 122. The channel 120 connects the dialysate line 78 (normally connected to the dialyzer input 79, as shown in FIG. 3) to a pre-dialyzer recirculation line 124. Similarly, the channel 122 connects the waste line 82 (normally connected to the dialyzer output 81, as shown in FIG. 3) to a post-dialyzer recirculation line 126. The bypass block 118 thus creates two separate recirculation loops, a pre-dialyzer loop 128 (FIG. 4) which includes the hydraulic elements "upstream" of the dialyzer 54, and a post-dialyzer loop 130 which includes the "downstream" hydraulic elements between the dialyzer 54 and the waste drain 86.

The dialysis machine 30 may be programmed for several different types of cleaning/disinfecting procedures to kill microorganisms attracted by the dialysate to the hydraulics flow path. These procedures include circulating only heated water, circulating a chemical solution, or circulating a heated chemical solution. If hot water alone is to be used, the heater 80 heats the water from the source 102 to a predetermined temperature. If a chemical solution is desired, the pumps 106 and 110 are respectively connected to sources 125 and 126 of cleaner and disinfectant (FIG. 4), as opposed to the bicarbonate and acid sources 104 and 108 (FIG. 3) to which the pumps are respectively connected during a typical dialysis procedure. The pumps 106 and 110 mix predetermined proportions of the cleaner and disinfectant with water from source 102 to create the required cleaning and/or disinfecting solutions. If a heated chemical solution is desired, the water from source 102 is heated by the heater 80 before it is mixed with the chemicals. Furthermore, a sterilant solution (not shown) may be added to the mixture by using an additional pump (not shown) to feed the sterilant into the line 78.

Once the hot water or the cleaning/disinfecting solution is prepared, it is recirculated through the pre-dialyzer recirculation loop 128 comprising the dialysate line 78, the channel 120 of the bypass block 118 and the pre-dialyzer recirculation line 124, as shown in FIG. 4. Additionally, a number of valves (collectively labeled with reference number 132) are controlled in a known manner to direct a flow of the cleaning solution from the pre-dialyzer recirculation loop 128 to the post-dialyzer recirculation loop 130 through bypass lines 134. Upon the conclusion of the cleaning/disinfecting process, the valves 132 are again operated in a known manner to direct the cleaning solution to the post-dialyzer recirculation loop 130 where a waste valve 136 disposes of the solution down the waste drain 86. If a chemical solution is used in the cleaning/disinfecting process, a final step of the process typically entails rinsing the dialysate hydraulics to ensure that the chemical cleaner 125 and disinfectant 126 are completely washed from the dialysate line 78 and the waste line 82 before those lines are connected to the dialyzer 54 as shown in FIG. 3.

The length of the cleaning/disinfecting process depends on whether the hot water is used alone or in combination with the chemical cleaner 125 and disinfectant 126 (or with a sterilant, not shown). If hot water alone is used, the length of the procedure will depend on the desired water temperature as the heater 80 must typically heat all the water used for the procedure. Additionally, a chemical solution will often be more effective the longer it is allowed to dwell within the respective recirculation loops 128 and 130. Thus, the length of time required to complete the cleaning/disinfecting process may vary from 30 minutes to several hours. This variance in time allows hospitals or clinics to utilize two different cleaning/disinfecting procedures. The first procedure requires an operator to perform a chemical clean/disinfect following the last patient treatment at the end of the day. The chemicals are then allowed to dwell within the hydraulic lines overnight before they are flushed from the system with a water rinse at the start of the next day. The other alternative is to perform the entire clean/disinfect procedure at the start of the day before the arrival of the first patient. Although it is preferred to clean the dialysate hydraulics at the start of the day (to kill any microorganisms which may have grown overnight), the present invention may be beneficially used with either procedure to reduce the time required to prepare the dialysis machine each morning.

The present invention includes a technique for programming the dialysis machine 30 to "wake-up" at a predetermined time each morning and automatically clean and disinfect the dialysate hydraulics before the dialysis machine operator arrives to set up and prime the blood tubing set. If the dialysis machine 30 was filled with a chemical cleaning/disinfecting solution after the last patient treatment, the machine 30 may be programmed to wake up and rinse the chemicals from the hydraulic lines. Alternatively, if the machine 30 has not been cleaned since the last patient treatment, the machine may be programmed to wake up at a relatively earlier time and perform the entire clean/disinfect procedure.

In addition to cleaning and disinfecting the dialysis machine 30 once a day, regulatory agencies typically require that the machine 30 undergo "power-up test" which checks the machine's electronic components to ensure that its memory is valid and that the microprocessor is able to execute all the instructions that will typically be required during a dialysis treatment. This power-up test is similar to the initial test performed by computers each time they are started or rebooted. Since the dialysis machine 30 needs to be idle during the power-up test (i.e., not performing a dialysis treatment or a cleaning or priming procedure), the machine 30 is preferably programmed to perform this test when it initially wakes up and before it begins any other "wake-up" procedure. Should the machine detect a problem during the power-up test, it will shut down and display an appropriate error message on the display 33 (FIG. 1) so that proper corrective action may be taken by the operator upon his or her arrival.

Once the machine 30 has passed the power-up test and has been cleaned and disinfected, it may automatically perform other "wake-up" procedures. For instance, if the machine had been previously disinfected and thus required only a rinse at wake-up, it may optionally begin preparing dialysate for use in the first dialysis treatment of the day (provided the proper connections to the bicarbonate and acid sources 104 and 108 have previously been made). Alternatively, upon the conclusion of the full clean/disinfect process, the machine 30 may enter a low-power mode and wait for an operator to initiate the procedure for priming the blood tubing set.

The machine 30 is preferably programmed at one time for the desired wake-up times (and the corresponding wake-up functions) for each day of the week. For example, the machine may be programmed through the touch screen monitor 33 as described more fully in the above-referenced U.S. Patent Application for a Graphical Operator Machine Interface and Method for Information Entry and Selection for a Dialysis Machine, assigned to the assignee hereof.

Figures 5, 6:
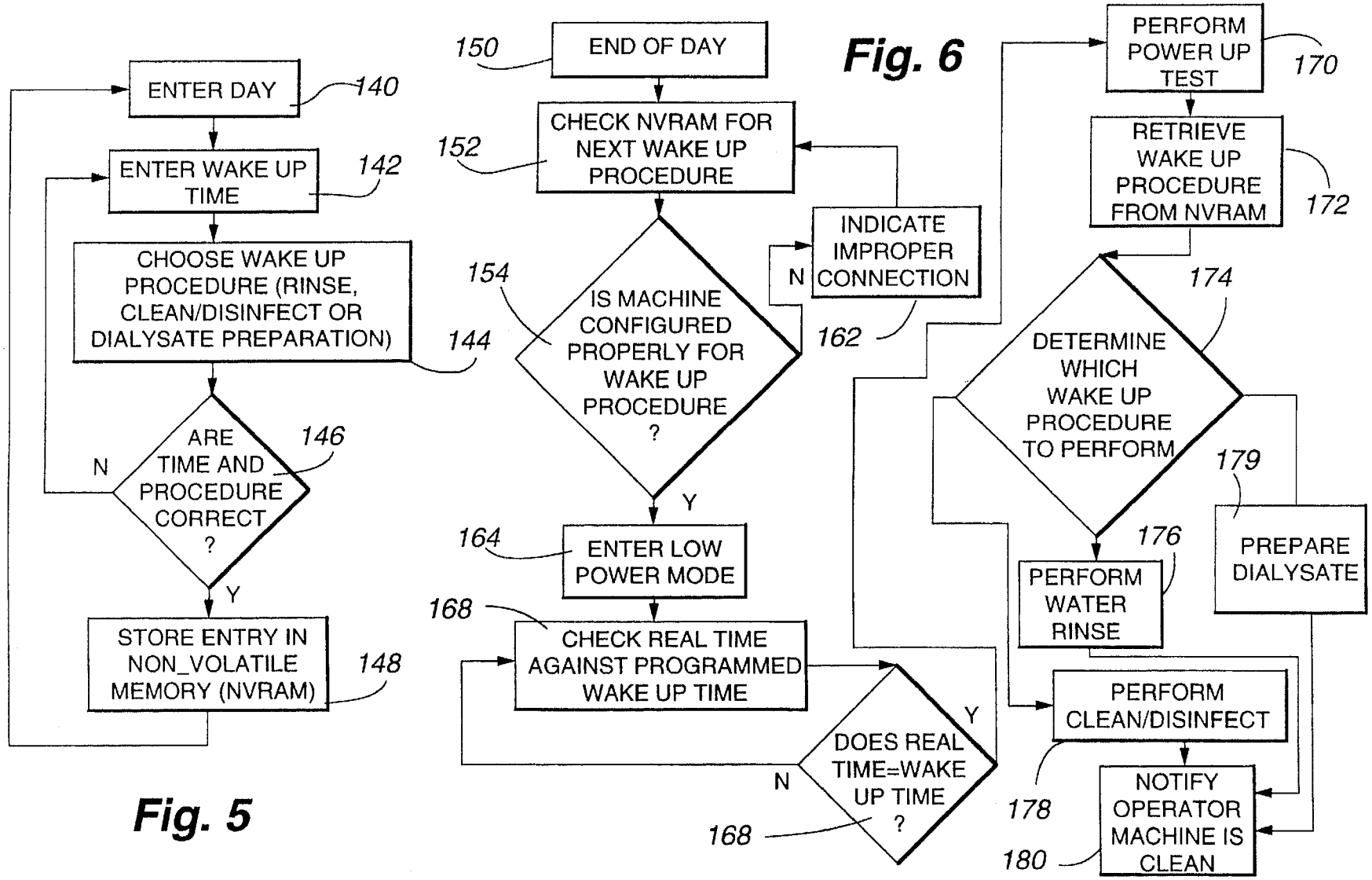
FIG. 5 is a flow chart illustrating the process of programming the dialysis machine shown in FIG. 1 to automatically wake up and conduct a cleaning/disinfecting procedure on the dialysate flow path according to the present invention.
FIG. 6 is flow chart illustrating the automated process of the present invention which is performed by the dialysis machine shown in FIG. 1 when it wakes up at a predetermined time and performs the cleaning/disinfecting procedure.

FIG. 5 illustrates a preferred method for programing the machine 30. An operator first selects at 140 the day of the week which will be programmed. The operator next enters at 142 the time the machine is to wake-up from a low power mode and initiate both the power-up test and the "wake-up" procedure. The operator next chooses at 144 the type of procedure which is to be performed. For example, if the clinic chooses to chemically clean and disinfect the dialysis machine 30 at the end of the day and allow the chemicals to dwell within the machine overnight, the operator would choose to perform only a water rinse at wake-up. The operator may also optionally prepare the machine as shown in Fig. 3 and program the machine to begin preparing dialysate upon completion of the rinse procedure. Alternatively, if the machine was not cleaned after the last patient treatment, the operator would choose to perform the entire cleaning and disinfecting process at wake-up.

After entering the day, time and type of procedure to be performed, the machine 30 preferably prompts the operator to confirm his or her choice at 146, at which point mistakes in either the wake-up time or the choice of procedure may be corrected. Once the entry is confirmed, the machine 30 stores the entry into its nonvolatile memory at 148 so that the information will not be lost in the case of a power loss. The machine 30 is then similarly programmed for the remaining days of the week, and the programmed information is retained in the machine's non-volatile memory until such time as the programmed information needs to be changed.

The process of placing the machine 30 in a low power or "sleep" mode and then waking the machine at the predetermined date and time is shown in FIG. 6. At the end of the day (i.e., after the last patient has been treated), the dialysis machine operator prepares the machine for the following day by either performing the chemical clean/disinfect procedure (and optionally preparing the machine for dialysate preparation), or by connecting the dialysate bypass block 118 as shown in FIG. 4 and connecting the pumps 106 and 108 to the sources 125 and 126 of cleaner and disinfectant, respectively. The operator then indicates to the machine at 150 (via the touch screen 33) that it is the end of the day. The machine 30 immediately checks its memory at 152 to determine what wake-up procedure it will be required to perform the following day. The machine 30 next conducts a connectivity check at 154 by polling several sensors connected within the dialysate hydraulics to determine whether the proper connections have been made to allow it to automatically perform the requested procedure without any additional human intervention. The sensors include a sensor 156 connected to Pump B (106) and a sensor 158 connected to Pump A (110) which indicate whether those pumps have been properly connected to the sources of cleaner and disinfectant 125 and 126 (or to the sources of bicarbonate and acid 104 and 108 if the machine is to wake up and prepare dialysate). Additionally, a sensor 160 determines whether the dialyzer bypass block 118 has been properly connected in place of the dialyzer 54. Furthermore, if a sterilant source and pump (not shown) are also used in cleaning the machine, an additional sensor (not shown) may be connected to the sterilant pump to ensure proper connectivity.

If the sensors indicate that a connection has been forgotten or incorrectly made, the machine 30 will immediately notify the operator at 162 of the problem (via the touch screen 33). This connectivity check is preferably done at the end of the day rather than at the wake-up time to prevent the machine from waking up before the arrival of any dialysis machine operators and discovering it was not properly connected for the desired procedure (thereby delaying the wake-up process and the time when the machine will be available for the first patient).

If the connectivity check confirms the proper connections have been made, the machine enters a low power mode at 164 to conserve energy until its preappointed wake up time. During the low power or "sleep" period, the machine periodically performs checks at 166 of the real time against the next programmed wake-up time stored in its memory. The machine then determines at 168 whether the wake-up time has been reached. If not, it loops back to 166 to continue performing the time checks. When the wake-up time is reached at 168, the machine performs the power-up test at 170. Alternatively, the machine 30 could perform the power-up test at a predetermined interval before the wake-up time (e.g., if the power-up test takes two minutes, the test could be performed two minutes before the wake-up time).

Upon conclusion of the power-up test at 170, the machine retrieves the desired wake up procedure from its non-volatile memory at 172. A determination is made at 174 as to which procedure is to be performed. If a water rinse has been programmed at 144, the machine 30 will initiate the rinse cycle at 176. If a clean/disinfect procedure has been programmed, the machine 30 will begin mixing the solution (or heating the water) at 178 as required to perform the procedure. Similarly, if the machine has been programmed to prepare dialysate, it will begin mixing the chemicals (FIG. 3) and heating the water at 179. Upon the conclusion of the wake-up procedure, the machine will notify the operator at 180 that the power-up test and the cleaning/disinfecting process have been successfully completed so that the bypass block 118 may be removed from the machine 30 in preparation for priming the dialyzer 54 and the blood tubing set.

The present invention thus represents a great savings in time to dialysis machine operators who must initially prepare a dialysis machine for patient treatment. For example, if a dialysis machine operator previously had to start work at 5:00 a.m. in order to clean and disinfect a number of dialysis machines before the arrival of patients at 8:00 a.m., those same machines could use the present invention to wake themselves up at 5:00 a.m. and automatically perform the clean and disinfect procedure. The operator would then only have to arrive early enough to prime the dialyzer and blood tubing set before connecting the dialysis machine to the first patient. The labor saved by the present invention thus represents a great savings in both time and costs for a hospital or a dialysis clinic.

A presently preferred embodiment of the present invention and many of its improvements have been described with a degree of particularity. This description is a preferred example of implementing the invention, and is not necessarily intended to limit the scope of the invention. The scope of the invention is defined by the following claims.

The invention claimed is:

1. A method of cleaning and disinfecting a dialysis machine with hot water, said dialysis machine including a dialysate preparation line and a waste disposal line adapted to be connected to a dialyzer, and said method comprising the steps of:

connecting a bypass line between the dialysate preparation line and the waste disposal line to transmit the heated water between the dialysate preparation and waste disposal lines;

connecting a first recirculation line to the dialysate preparation line and connecting a second recirculation line to the waste disposal line to recirculate the hot water through both the dialysate preparation and waste disposal lines; and programing the dialysis machine to perform the following steps at a predetermined date and time:

heating a supply of water;

pumping the heated water through the dialysate preparation line, the bypass line, the waste disposal line and each of the recirculation lines; and pumping the heated water down a waste drain within the waste disposal line to dispose of the heated water.

2. A method as defined in claim 1, wherein the dialysis machine is programmed to include an additional step of reducing power to the dialysis machine at the end of the day to conserve energy until the predetermined date and time.

3. A method as defined in claim 2, wherein the dialysis machine is programmed to include an additional step of conducting a diagnostic test prior to reducing power to the dialysis machine to ensure that the bypass and recirculation lines are properly connected.

4. A method as defined in claim 2, wherein the dialysis machine is programmed to include an additional step of performing a diagnostic test of a computer processor and memory system prior to heating the supply of water.

5. A method as defined in claim 1, wherein the dialysis machine is programmed to include an additional step of providing an indication that the dialysis machine has been cleaned and disinfected after the heated water has been disposed of down the waste drain.

6. A method as defined in claim 5, wherein the dialysis machine is programmed to include an additional step of reducing power to the dialysis machine after providing the indication that the dialysis machine has been cleaned and disinfected.

7. A method of cleaning and disinfecting a dialysis machine with a chemical solution, said dialysis machine including a dialysate preparation line and a waste disposal line adapted to be connected to a dialyzer, and said method comprising the steps of:

connecting a bypass line between the dialysate preparation line and the waste disposal line to transmit the chemical solution between the dialysate preparation and waste disposal lines;

connecting a first recirculation line to the dialysate preparation line and connecting a second recirculation line to the waste disposal line to recirculate the chemical solution through both the dialysate preparation and waste disposal lines;

connecting a chemical source to the dialysate preparation line; and programing the dialysis machine to perform the following steps at a predetermined date and time:

mixing chemicals from the chemical source with water from a water source to create the chemical solution within the dialysate preparation line;

pumping the chemical solution through the dialysate preparation line, the bypass line, the waste disposal line and each of the recirculation lines;

pumping the chemical solution down a waste drain within the waste disposal line to dispose of the chemical solution; and rinsing the dialysis machine with water to remove the chemicals from the dialysate preparation line, the bypass line, the waste disposal line and each of the recirculation lines.

8. A method as defined in claim 7, wherein the dialysis machine is programmed to include an additional step of reducing power to the dialysis machine at the end of the day to conserve energy until the predetermined date and time.

9. A method as defined in claim 8, wherein the dialysis machine is programmed to include an additional step of polling sensors connected to the chemical source and the recirculation lines prior to reducing power to the dialysis machine to ensure that the recirculation lines and the chemical source are properly connected.

10. A method as defined in claim 7, wherein the dialysis machine is programmed to include an additional step of allowing the chemical solution to dwell within the dialysate preparation line, the bypass line, the waste disposal line and each of the recirculation lines for a predetermined time before pumping the chemical solution down the waste drain.

11. A method as defined in claim 8, wherein the dialysis machine is programmed to include an additional step of performing a diagnostic test of a computer processor and memory system prior to mixing the chemicals and the water to create the chemical solution.

12. A method as defined in claim 7, wherein the dialysis machine is programmed to include an additional step of providing an indication that the dialysis machine has been cleaned and disinfected after the step of rinsing the dialysis machine with water.

13. A method as defined in claim 12, wherein the dialysis machine is programmed to include an additional step of reducing power to the dialysis machine after providing the indication that the dialysis machine has been cleaned and disinfected.

14. A method as defined in claim 7, wherein the dialysis machine is programmed to include an additional step of heating the water prior to mixing the chemicals with the water to create the chemical solution.

15. A method as defined in claim 7, wherein the steps prior to rinsing the dialysis machine with water are performed prior to the predetermined date and time.

16. A method as defined in claim 10, wherein the steps prior to rinsing the dialysis machine with water are performed prior to the predetermined date and time.

17. A method as defined in claim 16, wherein the dialysis machine is programmed to include an additional step of providing an indication that the dialysis machine has been cleaned and disinfected after the step of rinsing the dialysis machine with water.

* * * * *